United States Patent
Fletcher

(10) Patent No.: US 12,268,142 B2
(45) Date of Patent: Apr. 8, 2025

(54) CANNABIS VARIETY NWG 4113

(71) Applicant: NEW WEST GENETICS INC., Fort Collins, CO (US)

(72) Inventor: Richard S. Fletcher, Fort Collins, CO (US)

(73) Assignee: NEW WEST GENETICS INC., Fort Collins, CO (US)

(*) Notice: Subject to any disclaimer, the term of this patent is extended or adjusted under 35 U.S.C. 154(b) by 349 days.

(21) Appl. No.: 17/659,425

(22) Filed: Apr. 15, 2022

(65) Prior Publication Data

US 2023/0329175 A1    Oct. 19, 2023

(51) Int. Cl.
  *A01H 5/12*    (2018.01)
  *A01H 6/28*    (2018.01)

(52) U.S. Cl.
  CPC .............. *A01H 6/28* (2018.05); *A01H 5/12* (2013.01)

(58) Field of Classification Search
  CPC ...................................................... A01H 6/28
  See application file for complete search history.

(56) References Cited

U.S. PATENT DOCUMENTS

| | | | |
|---|---|---|---|
| 10,499,584 B2 * | 12/2019 | Fletcher | .............. C12C 7/28 |
| 11,304,393 B2 | 4/2022 | Fletcher et al. | |
| 2021/0386031 A1 | 12/2021 | Elkins et al. | |
| 2021/0396473 A1 | 12/2021 | Gotlind et al. | |

OTHER PUBLICATIONS

UPOV publication TG/276/1 Rev., Hemp: Guidelines for the Conduct of Tests for Distinctness, Uniformity and Stability; Date: Mar. 28, 2012 + Oct. 26, 2021, 29 pages. (Year: 2012).*

* cited by examiner

*Primary Examiner* — Russell Kallis
(74) *Attorney, Agent, or Firm* — McKee, Voorhees & Sease, PLC

(57) ABSTRACT

A novel Cannabis variety designated NWG 4113 is provided. This disclosure thus relates to the seeds of Cannabis variety NWG 4113, to the plants of Cannabis variety NWG 4113, to plant parts of Cannabis variety NWG 4113, to methods for producing a Cannabis plant by crossing a plant of Cannabis variety NWG 4113 with a plant of another Cannabis variety, and to methods for producing a plant of Cannabis variety NWG 4113 containing in its genetic material one or more backcross conversion traits or transgenes and to the backcross conversion Cannabis plants and plant parts produced by those methods.

29 Claims, No Drawings

CANNABIS VARIETY NWG 4113

TECHNICAL FIELD

The present disclosure relates to the field of plant breeding. In particular, this disclosure relates to a new Cannabis variety designated NWG 4113.

BACKGROUND

Industrial hemp is legally defined in the United States as Cannabis which contains 0.3% or less total sample dry weight of Δ9-Tetrahydrocannabinal (THC). THC content is normally well above the 0.30% threshold in modern varieties of Cannabis. THC is one of an estimated 85 cannabinoids (a class of terpenoids) synthesized in Cannabis species. The demand for the medicinal properties of cannabinoids derived from Cannabis is growing. The medicinal effects of cannabinoids on human health continue to be validated as clinical research in this field expands and gains traction. The ability to create this medicine without THC is highly desired by many patients and regulatory agencies.

A vast majority of the Cannabis produced in the United States is done so by clonal propagation. Under this production scheme, meristems are cut from a selected plant and treated by various methods to induce rooting so that many, genetically identical progeny may be derived from the original. This is primarily done because breeding Cannabis seeds which consistently express a particular cannabinoid profile, often elevated for a particular cannabinoid (e.g. THC), is generally regarded as difficult. The simplicity of breeding varieties to be produced under a clonal reproduction system is quickly offset by the cost of clonal production, among other factors. There is a continuing need in the industry for industrial hemp varieties which are reliably low in THC when produced in diverse environmental conditions and which express elevated levels of certain other cannabinoids.

There are numerous steps in the development of any novel, desirable plant germplasm. Plant breeding preferably begins with the analysis and definition of problems and weaknesses of the current germplasm, the establishment of program goals, and the definition of specific breeding objectives. The next step is preferable selection of germplasm that possess the traits to meet the program goals. The goal is to combine in a single variety or hybrid an improved combination of desirable traits from the parental germplasm.

SUMMARY

There is provided a novel Cannabis variety designated NWG 4113. This disclosure thus relates to the seeds of Cannabis variety NWG 4113, to the plants of Cannabis variety NWG 4113, to plant parts of Cannabis variety NWG 4113, to methods for producing a Cannabis variety produced by crossing the Cannabis variety NWG 4113 with itself or with another Cannabis variety, and to methods for producing a Cannabis variety containing in its genetic material one or more backcross conversion traits or transgenes and to the backcross conversion Cannabis plants and plant parts produced by those methods. This disclosure further relates to hybrid Cannabis seeds and plants produced by crossing Cannabis variety NWG 4113 with another Cannabis variety. This disclosure also relates to Cannabis varieties and plant parts derived from Cannabis variety NWG 4113, to methods for producing other Cannabis varieties derived from Cannabis variety NWG 4113 and to the Cannabis varieties and their parts derived using those methods. Also provided are Cannabis plants having the physiological and morphological characteristics of Cannabis variety NWG 4113.

In another aspect, the present disclosure provides regenerable cells for use in tissue culture of Cannabis variety NWG 4113. The tissue culture will preferably be capable of regenerating plants having essentially all of the physiological and morphological characteristics of the foregoing Cannabis plant, and of regenerating plants having substantially the same genotype as the foregoing Cannabis plant. Still further, the present disclosure provides Cannabis plants regenerated from the tissue cultures disclosed herein.

The disclosure also relates to methods for producing a Cannabis plant containing in its genetic material one or more transgenes and to the transgenic Cannabis plant produced by those methods.

Another aspect of the disclosure is a Cannabis plant further comprising a single locus conversion. In one embodiment, the Cannabis plant is defined as comprising the single locus conversion and otherwise capable of expressing all of the morphological and physiological characteristics of the Cannabis variety NWG 4113. In particular embodiments, the single locus conversion may comprise a transgenic gene which has been introduced by genetic transformation into the Cannabis variety NWG 4113 or a progenitor thereof. A transgenic or non-transgenic single locus conversion can also be introduced by backcrossing, as is well known in the art. In still other embodiments of the disclosure, the single locus conversion may comprise a dominant or recessive allele. The locus conversion may confer potentially any trait upon the single locus converted plant, including herbicide resistance, insect or pest resistance, resistance to bacterial, fungal, or viral disease, modified oil content, modified terpene or cannabinoid content, and industrial usage. The trait may be, for example, conferred by a naturally occurring gene introduced into the genome of the variety by backcrossing, a natural or induced mutation, or a transgene introduced through genetic transformation techniques into the plant or a progenitor of any previous generation thereof. When introduced through transformation, a genetic locus may comprise one or more transgenes integrated at a single chromosomal location.

The disclosure further relates to methods for genetically modifying a Cannabis plant of the Cannabis variety NWG 4113 and to the modified Cannabis plant produced by those methods. The genetic modification methods may include, but are not limited to mutation, genome editing, RNA interference, gene silencing, backcross conversion, genetic transformation, single and multiple gene conversion, and/or direct gene transfer. The disclosure further relates to a genetically modified Cannabis plant produced by the above methods, wherein the genetically modified Cannabis plant comprises the genetic modification and otherwise comprises all of the physiological and morphological characteristics of Cannabis variety NWG 4113.

In still yet another aspect, the genetic complement of the Cannabis variety NWG 4113 is provided. The phrase "genetic complement" is used to refer to the aggregate of nucleotide sequences, the expression of which sequences defines the phenotype of, in the present case, a Cannabis plant, or a cell or tissue of that plant. A genetic complement thus represents the genetic makeup of a cell, tissue or plant, and a hybrid genetic complement represents the genetic makeup of a hybrid cell, tissue or plant. The disclosure thus provides Cannabis plant cells that have a genetic complement in accordance with the Cannabis plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles.

In still yet another aspect, the disclosure provides a method of determining the genotype of a plant of Cannabis variety NWG 4113 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The disclosure further provides a computer readable medium produced by such a method.

This disclosure further relates to the $F_1$ hybrid Cannabis plants and plant parts grown from the hybrid seed produced by crossing Cannabis variety NWG 4113 to a second Cannabis plant. Still further included in the disclosure are the seeds of an $F_1$ hybrid plant produced with the Cannabis variety NWG 4113 as one parent, the second generation ($F_2$) hybrid Cannabis plant grown from the seed of the $F_1$ hybrid plant, and the seeds of the $F_2$ hybrid plant. Thus, any such methods using the Cannabis variety NWG 4113 are part of this disclosure: selfing, backcrosses, hybrid production, crosses to populations, and the like. All plants produced using Cannabis variety NWG 4113 as at least one parent are within the scope of this disclosure. Advantageously, the Cannabis variety could be used in crosses with other, different, Cannabis plants to produce first generation ($F_1$) Cannabis hybrid seeds and plants with superior characteristics. Newly developed $F_1$ hybrids can be reproduced via asexual reproduction.

The disclosure further provides methods for developing a Cannabis variety in a Cannabis plant breeding program using plant breeding techniques including but not limited to recurrent selection, backcrossing, pedigree breeding, restriction fragment length polymorphism enhanced selection, genetic marker enhanced selection, and transformation. Seeds, Cannabis plants, and parts thereof, produced by such breeding methods are also part of the disclosure.

This disclosure also relates to Cannabis plants or breeding cultivars and plant parts derived from Cannabis variety NWG 4113. Still yet another aspect of the disclosure is a method of producing a Cannabis plant derived from the Cannabis variety NWG 4113, the method comprising the steps of: (a) preparing a progeny plant derived from Cannabis variety NWG 4113 by crossing a plant of the Cannabis variety NWG 4113 with a second Cannabis plant; and (b) crossing the progeny plant with itself or a second plant to produce a seed of a progeny plant of a subsequent generation which is derived from a plant of the Cannabis variety NWG 4113. In further embodiments of the disclosure, the method may additionally comprise: (c) growing a progeny plant of a subsequent generation from the seed of a progeny plant of a subsequent generation and crossing the progeny plant of a subsequent generation with itself or a second plant; and repeating the steps for an additional 2-10 generations to produce a Cannabis plant derived from the Cannabis variety NWG 4113. The plant derived from Cannabis variety NWG 4113 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from Cannabis variety NWG 4113 is obtained which possesses some of the desirable traits of the line as well as potentially other selected traits. Also provided by the disclosure is a plant produced by this and the other methods of the disclosure.

In another embodiment, the method of producing a Cannabis plant derived from the Cannabis variety NWG 4113 further comprises: (a) crossing the Cannabis variety NWG 4113-derived Cannabis plant with itself or another Cannabis plant to yield additional Cannabis variety NWG 4113-derived progeny Cannabis seed; (b) growing the progeny Cannabis seed of step (a) under plant growth conditions to yield additional Cannabis variety NWG 4113-derived Cannabis plants; and (c) repeating the crossing and growing steps of (a) and (b) to generate further Cannabis variety NWG 4113-derived Cannabis plants. In specific embodiments, steps (a) and (b) may be repeated at least 1, 2, 3, 4, or 5 or more times as desired. The disclosure still further provides a Cannabis plant produced by this and the foregoing methods.

The disclosure also provides methods of multiplication or propagation of Cannabis plants of the disclosure, which can be accomplished using any method known in the art, for example, via vegetative propagation and/or seed. Still further, as another aspect, the disclosure provides a method of vegetatively propagating a plant of Cannabis variety NWG 4113. In a non-limiting example, the method comprises: (a) collecting a plant part capable of being propagated from a plant of Cannabis variety NWG 4113; (b) producing at least a first rooted plant from the plant part. The disclosure also encompasses the plantlets and plants produced by these methods.

DETAILED DESCRIPTION

In the description and tables which follow, a number of terms are used. In order to provide a clear and consistent understanding of the present disclosure, the following definitions are provided:

An "allele" is any of one or more alternative forms of a genetic sequence. In a diploid cell or organism, the two alleles of a given genetic sequence occupy corresponding loci on a pair of homologous chromosomes.

The term "backcrossing" refers to a process in which a breeder crosses progeny back to one of the parents one or more times, for example, a first generation hybrid $F_1$ with one of the parental genotype of the $F_1$ hybrid.

A "cell" as used herein includes a plant cell, whether isolated, in tissue culture or incorporated in a plant or plant part. The cell can be a cell, such as a somatic cell, of the variety having the same set of chromosomes as the cells of the deposited seed, or, if the cell contains a locus conversion or transgene, otherwise having the same or essentially the same set of chromosomes as the cells of the deposited seed.

A "clone" refers to a plantlet cutting that is removed from another, healthy *cannabis* plant. Tissue is collected from the stem and shoot sections of the healthy *cannabis* plant, and generally consists of at least (3-4) nodes and one apical meristem.

A "commodity plant product" refers to any composition or product that is comprised of material derived from a plant, seed, plant cell, or plant part of the present disclosure. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, fiber, crushed of whole grain, and any other food for human or animal consumption; biomasses and fuel products; and raw material in industry.

As used herein, "genome editing" refers to a type of genetic engineering in which DNA is inserted, replaced, modified, or removed from a genome using artificially engineered nucleases or other targeted changes using homologous recombination. Examples include but are not limited to use of zinc finger nucleases (ZFNs), TAL effector nucleases (TALENs), meganucleases, CRISPR/Cas9, and other CRISPR related technologies.

A "locus conversion" (also called a "trait conversion" or "gene conversion") refers to a plant or plants within a variety or line that have been modified in a manner that retains the overall genetics of the variety and further comprises one or more loci with a specific desired trait, such as but not limited to insect or pest control, disease control or herbicide tolerance. Examples of single locus conversions include mutant genes, transgenes and native traits finely mapped to a single locus. One or more locus conversion traits may be introduced into a single cultivar.

As used herein, the term "plant" includes plant cells, plant protoplasts, plant tissue, plant cells of tissue culture from which Cannabis plants can be regenerated, plant calli, plant clumps, and plant cells that are intact in plants, or parts of plants such as pollen, flowers, seeds, leaves, stems, and the like.

As used herein, the term "plant part" refers to any part, organ, tissue, or cell of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots". A plant part may also include certain extracts such as kief or hash which includes cannabis trichomes or glands.

As used herein, the term "progeny" refers to any plant resulting from a vegetative or sexual reproduction from one or more parent plants or descendants thereof. For instance, a progeny plant may be obtained by cloning or selfing of a parent plant or by crossing two parent plants and include selfings as well as the F1 or F2 or still further generations. An F1 is a first-generation progeny produced from parents at least one of which is used for the first time as donor of a trait, while offspring of second generation (F2) or subsequent generations (F3, F4, etc.) are specimens produced from selfings of F1's F2's etc. An F1 may thus be (and usually is) a hybrid resulting from a cross between two true breeding parents (true-breeding is homozygous for a trait), while an F2 may be (and usually is) a progeny resulting from self-pollination of said F1 hybrids.

A "single locus converted" plant refers to plants which are developed by a plant breeding technique called backcrossing or via genetic engineering wherein essentially all of the morphological and physiological characteristics of a variety are recovered in addition to the desired trait or characteristics conferred by the single locus transferred into the variety via the backcrossing technique or via genetic engineering. A single locus may comprise one gene, or in the case of transgenic plants, one or more transgenes integrated into the host genome at a single site (locus).

A "transgene" refers to a nucleic acid of interest that can be introduced into the genome of a plant by genetic engineering techniques (e.g., transformation).

As used herein, "vegetative propagation" refers to asexual propagation of a plant that is accomplished by, for example, taking and propagating cuttings, by grafting or budding, by layering, by division of plants, or by separation of specialized structure, such as stem, roots, tubers, rhizomes, or bulbs.

Cannabis Variety NWG 4113

A description of Cannabis variety NWG 4113 is provided in Table 1. The plant variety descriptors in Table 1 refer to those described for hemp in the "Objective Description of Variety Hemp (Cannabis sativa L.)-Exhibit C" as published by the U.S. Department of Agriculture, Agricultural Marketing Service, Science and Technology, Plant Variety Protection Office.

TABLE 1

| PLANT | |
|---|---|
| Less than 0.3% delta-9 tetrahydrocannabinol (THC) concentration level on a dry weight basis | Yes |
| Plant Type | Sexually Propagated |
| Proportion of Hermaphrodite (Bisexual) Plants | Low (<5%) |
| Proportion of Female Plants | Medium (36-65%) |
| Proportion of Male Plants | Medium (36-65%) |
| Natural Plant Height (At Flowering) | 140 to 260 cm |
| Branching | Weak |
| SEEDLING | |
| Cotyledon Shape | Medium Obovate |
| Cotyledon Color | Medium Green |
| Hypocotyl Intensity of Anthocyanin Coloration | Weak |
| STEM | (At Internode Below Last Opposite Leaves on Female or Monoecious Plants) |
| Color | Medium Green |
| Length of Internode | 7.9 cm |
| Thickness | Medium |
| Depth of Grooves | Shallow |
| Pith in Cross-Section | Medium |
| Anthocyanin Coloration of Crown | Absent |
| LEAVES | (Last-Formed Opposite; Fully Expanded |

TABLE 1-continued

| | Leaves, After Flowering) |
|---|---|
| Intensity of Green Color | Medium |
| Length of Petiole | Medium |
| Length of Petiole | 8.6 cm |
| Anthocyanin Color in Petiole | Absent |
| Number of Leaflets | Medium (Majority = 7) |
| Central Leaflet Length | 17.7 cm |
| Central Leaflet Width | 18.2 cm |
| INFLORESCENCE | |
| Time of Male Flowering | Medium |
| Flowering Date (Male) Number of Days (Julian) | Day 209, if planted on or near day 153 |
| Male Flowers Anthocyanin Coloration | Absent |
| Inflorescence THC Content | Absent or Very Low |
| SEED | |
| 1000 Seed Weight | 14.5 g |
| Color of Testa | 156A RHS |
| Marbling of Color | Weak |
| Shape | Ovate |

Tables 2 and 3 provide a comparison of NWG 4113 and Fedora17 (a check variety for UPOV Tests of Uniformity, Stability and Distinctness). Quantitative data were collected from measurements on 20 plants. Table 2 shows data collected from 3 replicate plots (60 sqft; 15" row spacing) grown Northeast of Wellington, CO in 2019. Table 3 shows data collected from 2 replicate plots (60 sqft; 30" row spacing) grown near Windsor, CO in 2020. Plant size was larger for all genotypes in 2020 including Fedora17. This was due to two factors which lowered overall plant density which is known to increase plant size in hemp: row spacing was changed from 15" in 2019 to 30" in 2020; and a small hail event on Jun. 11, 2020 mortally wounded about 25% of seedlings.

NWG 4113 has shown stable uniformity relative to Fedora over 2 generations. Variants can be expected at <1% when plant populations exceed 120,000 plants per acre: male and female plants with higher-than-average number of branches at top of plant, particularly on field margins.

Tables 4, 5, and 6 provide a comparison of NWG 4113, NWG 2463, and NWG 4000. They are consistently and significantly differentiated from each other by their plant height at maturity where NWG 4000<NWG 2463<NWG 4113. NWG 4113 is significantly differentiated from NWG 4000 and NWG 2463 by its flowering time (days after planting) where NWG 4113 flowers >1.5 days later. Further, NWG 4113 produces significantly higher average CBD content than NWG 2463 or NWG 4000, with a maximum CBD content of 7.6%.

Table 4 shows data collected from 2 replicate plots (60 sq ft; 30" row spacing) grown near Windsor, CO in 2020. Table 5 shows plant height at maturity measured in plots (90 sq ft) planted on 12.5" row spacing at 1" and 2" in-row seed spacing, 4-5 replicates per variety per treatment. Trials conducted near Wellington, CO in 2021. Table 6 shows average cannabinoid content (% THC and % CBD) measured on 60 plants per plot, 3 plots per location, 4 locations in Canada (La Salle, MB; Carman, MB; Russell, MB; Coaldale, AB) in 2021. Samples were collected approximately 30 days prior to maturity according to the "Policy for the Management of Industrial Hemp Varieties on the List of Approved Cultivars" that came into effect on Mar. 11, 2020.

TABLE 2

| Trait | NWG 4113 | s.d. | Fedora17 | s.d. | t-test p-value | t-value |
|---|---|---|---|---|---|---|
| Cotyledon Shape | Medium | — | Broad | — | — | — |
| Proportion of Hermaphrodite Plants | Low | — | High | — | — | — |
| Proportion of Male Plants | Medium | — | Low | — | — | — |
| Plant Height (m) | 1.45 | 0.24 | 1.29 | 0.18 | 0.04 | 2.15 |
| Main Stem Thickness (cm) | 1.23 | 0.36 | 0.71 | 0.20 | <0.0001 | 5.78 |

TABLE 3

| Trait | NWG 4113 | s.d. | Fedora17 | s.d. | t-test p-value | t-value |
|---|---|---|---|---|---|---|
| Cotyledon Shape | Medium | — | Broad | — | — | — |
| Proportion of Hermaphrodite Plants | Low | — | High | — | — | — |
| Proportion of Male Plants | Medium | — | Low | — | — | — |
| Plant Height (m) | 2.17 | 0.34 | 1.84 | 0.43 | 0.03 | 2.47 |
| Main Stem Thickness (cm) | 2.0 | 0.48 | 1.5 | 0.28 | 0.02 | 2.52 |

TABLE 4

| Variety | Petiole Length (mm)* | Central Leaflet Length (mm)† | Central Leaflet Width (mm)* | Plant Height (m)* | Length of Internode (mm)* | Main Stem Thickness (mm)* |
| --- | --- | --- | --- | --- | --- | --- |
| NWG 2730 | 112.9 ab | 168.4 c | 21.3 a | 2.27 a | 62.9 b | 27.6 a |
| NWG 4113 | 116 a | 177.9 bc | 20.6 ab | 2.17 ab | 77.2 a | 21.3 b |
| NWG 2463 | 100.8 ab | 187.7 a | 20.1 ab | 2.05 ab | 81.1 a | 20.7 b |
| NWG 4000 | 94.3 b | 172.8 bc | 18.3 b | 1.99 b | 76.9 a | 18.9 b |
| Fedora17 | 68.7 c | 151.9 d | 18.2 b | 1.76 c | 83.5 a | 15 c |

*$\alpha = 0.05$,
†$\alpha = 0.10$

TABLE 5

| | Height (m) | |
| --- | --- | --- |
| Variety | 2" seed spacing | 1" seed spacing |
| 2730 | 2.19 a | 2.07 a |
| 4113 | 2.12 b | 1.91 b |
| 2463 | 1.95 c | 1.82 c |
| 4000 | 1.85 d | 1.73 d |

$\alpha = 0.05$

TABLE 6

| Variety | % THC (s.d., max) | % CBD (s.d., max) |
| --- | --- | --- |
| 4113 | 0.13 (0.03, 0.23) a | 5.7 (1.2, 7.6) a |
| 2463 | 0.13 (0.03, 0.17) a | 4.9 (0.64, 6.2) b |
| 4000 | 0.13 (0.03, 0.18) a | 4.8 (1.2, 7.0) b |

$\alpha = 0.10$

Further Embodiments

The disclosure provides methods and compositions relating to plants, seeds and derivatives of a new Cannabis variety herein referred to as Cannabis variety NWG 4113.

There are numerous steps in the development of any novel plant with desirable characteristics. Selection of traits is a very important aspect of plant breeding. Once desirable traits are identified, the plants with those desirable traits are crossed in order to recombine the desirable traits and through selection, varieties or parent lines are developed. Choice of breeding or selection methods depends on the mode of plant reproduction, the heritability of the trait(s) being improved, and the type of cultivar used commercially (e.g., $F_1$ hybrid cultivar, pureline cultivar, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach is used extensively for breeding, for example, disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Pedigree breeding is used commonly for the improvement of self-pollinating crops or inbred lines of cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new cultivars.

Mass and recurrent selections may be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant may also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. SSR technology is currently the most efficient and practical marker technology; more marker loci may be routinely used and more alleles per marker locus may be found using SSRs in comparison to RFLPs. SNPs may also be used to identify the unique genetic composition of the disclosure and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select toward the genome of the recurrent parent and against the markers of the donor parent. This procedure attempts to minimize the amount of genome from the donor parent that remains in the selected plants. It may also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into Cannabis varieties. Mutations that occur spontaneously or are artificially induced may be useful sources of variability for a plant breeder. The goal of artificial mutagenesis is to increase the rate of mutation for a desired characteristic. Mutation rates may be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding may be found in Principles of Cultivar Development by Fehr, Macmillan Publishing Company, 1993.

The production of double haploids may also be used for the development of homozygous lines in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Cannabis is an important and valuable crop. Thus, a continuing goal of Cannabis plant breeders is to develop stable, high yielding Cannabis varieties that are agronomically sound. To accomplish this goal, the Cannabis breeder preferably selects and develops Cannabis plants with traits that result in superior varieties.

This disclosure also is directed to methods for producing a Cannabis plant by crossing a first parent Cannabis plant with a second parent Cannabis plant wherein either the first or second parent Cannabis plant is a Cannabis plant of the variety NWG 4113. Further, both first and second parent Cannabis plants can come from the variety NWG 4113. Still further, this disclosure also is directed to methods for producing a NWG 4113-derived Cannabis plant by crossing variety NWG 4113 with a second Cannabis plant and growing the progeny seed and repeating the crossing and growing steps with the NWG 4113-derived plant from 0 to 7 times. Thus, any such methods using the variety NWG 4113 are part of this disclosure: selfing, backcrosses, hybrid production, crosses to populations, and the like. All plants produced using variety NWG 4113 as a parent are within the scope of this disclosure, including plants derived from variety NWG 4113. Advantageously, the variety may be used in crosses with other, different, varieties to produce first generation ($F_1$) Cannabis seeds and plants with superior characteristics.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. In some embodiments, a transgenic variant of Cannabis variety NWG 4113 may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last 15 to 20 years several methods for producing transgenic plants have been developed, and the present disclosure also relates to transgenic variants of Cannabis variety NWG 4113.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least approximately 1000 nucleotides of sequence upstream from the 5' end of the coding region and at least approximately 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the disclosure may be produced by any means, including genomic preparations, cDNA preparations, in vitro synthesis, RT-PCR, and in vitro or in vivo transcription.

One embodiment of the disclosure is a process for producing Cannabis variety NWG 4113 further comprising a desired trait, the process comprising introducing a transgene that confers a desired trait to a Cannabis plant of variety NWG 4113. Another embodiment is the product produced by this process. In one embodiment, the desired trait may be one or more of herbicide resistance, insect resistance, disease resistance, male sterility, modified oil content, or modified terpene or cannabinoid content. The specific gene may be any known in the art or listed herein.

Numerous methods for plant transformation have been developed, including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993), and Armstrong, "The First Decade of Maize Transformation: A Review and Future Perspective," Maydica, 44:101-109 (1999). In addition, expression vectors and in vitro culture methods for plant cell or tissue transformation and regeneration of plants are available. See, for example, Gruber et al., "Vectors for Plant Transformation," in *Methods in Plant Molecular Biology and Biotechnology*, Glick and Thompson Eds., CRC Press, Inc., Boca Raton, pp. 89-119 (1993).

A genetic trait which has been engineered into the genome of a particular Cannabis plant may then be moved into the genome of another cultivar using traditional breeding techniques that are well known in the plant breeding arts. For example, a backcrossing approach is used to move a transgene from a transformed Cannabis variety into an already developed Cannabis variety, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Included among various plant transformation techniques are methods that permit the site-specific modification of a plant genome, including coding sequences, regulatory elements, non-coding and other DNA sequences in a plant genome. Such methods are well-known in the art and include, for example, use of the CRISPR-Cas system, zinc-finger nucleases (ZFNs), and transcription activator-like effector nucleases (TALENs), among others.

Plant transformation may involve the construction of an expression vector which will function in plant cells. Such a vector can comprise DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed Cannabis plants using transformation methods as described below to incorporate transgenes into the genetic material of the Cannabis plant(s).

Expression Vectors for Cannabis Transformation: Marker Genes

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., *Plant Physiol.,* 86:1216 (1988); Jones et al., *Mol. Gen. Genet.,* 210:86 (1987); Svab et al., *Plant Mol. Biol.,* 14:197 (1990); Hille et al., *Plant Mol. Biol.,* 7:171 (1986)). Other selectable marker genes confer resistance to herbicides such as glyphosate, glufosinate, or bromoxynil (Comai et al., *Nature,* 317:741-744 (1985); Gordon-Kamm et al., *Plant Cell,* 2:603-618 (1990); Stalke et al., *Science,* 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz et al., *Somatic Cell Mol. Genet.,* 13:67 (1987); Shah et al., *Science,* 233:478 (1986); Charest et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri et al., *EMBO J.,* 8:343 (1989); Koncz et al., *Proc. Natl. Acad. Sci. USA,* 84:131 (1987); DeBlock et al., *EMBO J.,* 3:1681 (1984)).

In vivo methods for visualizing GUS activity that do not require destruction of plant tissue are available (Molecular Probes, Publication 2908, IMAGENE GREEN, pp. 1-4 (1993); Naleway et al., *J. Cell Biol.*, 115:151a (1991)). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science*, 263:802 (1994)). GFP and mutants of GFP may be used as screenable markers.

Expression Vectors for Cannabis Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in Cannabis. Optionally, the inducible promoter is operably linked to a nucleotide sequence encoding a signal sequence which is operably linked to a gene for expression in Cannabis. With an inducible promoter the rate of transcription increases in response to an inducing agent.

Any inducible promoter can be used. See, Ward et al., *Plant Mol. Biol.*, 22:361-366 (1993). Exemplary inducible promoters include, but are not limited to, that from the ACEI system which responds to copper (Mett et al., *Proc. Natl. Acad. Sci. USA*, 90:4567-4571 (1993)); In2 gene from maize which responds to benzenesulfonamide herbicide safeners (Hershey et al., *Mol. Gen Genetics*, 227:229-237 (1991); Gatz et al., *Mol. Gen. Genetics*, 243:32-38 (1994)); or Tet repressor from Tn10 (Gatz et al., *Mol. Gen. Genetics*, 227:229-237 (1991)). A particularly preferred inducible promoter is a promoter that responds to an inducing agent to which plants do not normally respond. An exemplary inducible promoter is the inducible promoter from a steroid hormone gene, glucocorticoid response elements, the transcriptional activity of which is induced by a glucocorticoid hormone (Schena et al., *Proc. Natl. Acad. Sci. USA*, 88:10421-10425 (1991)).

B. Constitutive Promoters—A constitutive promoter is operably linked to a gene for expression in Cannabis or the constitutive promoter is operably linked to a nucleotide sequence encoding a signal sequence which is operably linked to a gene for expression in Cannabis.

Many different constitutive promoters can be utilized. Exemplary constitutive promoters include, but are not limited to, the promoters from plant viruses such as the 35S promoter from CaMV (Odell et al., *Nature*, 313:810-812 (1985)) and the promoters from such genes as rice actin (McElroy et al., *Plant Cell*, 2: 163-171 (1990)); ubiquitin (Christensen et al., *Plant Mol. Biol.*, 12:619-632 (1989); Christensen et al., *Plant Mol. Biol.*, 18:675-689 (1992)); pEMU (Last et al., *Theor. Appl. Genet.*, 81:581-588 (1991)); MAS (Velten et al., *EMBO* 1, 3:2723-2730 (1984)); and maize H3 histone (Lepetit et al., *Mol. Gen. Genetics*, 231: 276-285 (1992); Atanassova et al., *Plant Journal*, 2 (3): 291-300 (1992)). The ALS promoter, an Xba1/Nco1 fragment 5' to the *Brassica napus* ALS3 structural gene (or a nucleotide sequence similarity to said Xba1/Nco1 fragment), represents a particularly useful constitutive promoter. See PCT Application WO 96/30530.

C. Tissue-Specific or Tissue-Preferred Promoters—A tissue-specific promoter is operably linked to a gene for expression in Cannabis. Optionally, the tissue-specific promoter is operably linked to a nucleotide sequence encoding a signal sequence which is operably linked to a gene for expression in Cannabis. Plants transformed with a gene of interest operably linked to a tissue-specific promoter produce the protein product of the transgene exclusively, or preferentially, in a specific tissue.

Any tissue-specific or tissue-preferred promoter can be utilized. Exemplary tissue-specific or tissue-preferred promoters include, but are not limited to, a root-preferred promoter such as that from the phaseolin gene (Murai et al., *Science*, 23:476-482 (1983); Sengupta-Gopalan et al., *Proc. Natl. Acad. Sci. USA*, 82:3320-3324 (1985)); a leaf-specific and light-induced promoter such as that from cab or rubisco (Simpson et al., *EMBO J.*, 4(11):2723-2729 (1985); Timko et al., *Nature*, 318:579-582 (1985)); an anther-specific promoter such as that from LAT52 (Twell et al., *Mol. Gen. Genetics*, 217:240-245 (1989)); a pollen-specific promoter such as that from Zm13 (Guerrero et al., *Mol. Gen. Genetics*, 244:161-168 (1993)); or a microspore-preferred promoter such as that from apg (Twell et al., *Sex. Plant Reprod.*, 6:217-224 (1993)).

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.*, 20:49 (1992); Knox, C. et al., *Plant Mol. Biol.*, 9:3-17 (1987); Lerner et al., *Plant Physiol.*, 91:124-129 (1989); Frontes et al., *Plant Cell*, 3:483-496 (1991); Matsuoka et al., *Proc. Natl. Acad. Sci.*, 88:834 (1991); Gould et al., *J. Cell. Biol.*, 108:1657 (1989); Creissen et al., *Plant J.*, 2:129

(1991); Kalderon et al., *Cell,* 39:499-509 (1984); Steifel et al., *Plant Cell,* 2:785-793 (1990).

Foreign Protein Genes and Agronomic Genes

With transgenic plants according to the present disclosure, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.,* 114:92-6 (1981).

According to a preferred embodiment, the transgenic plant provided for commercial production of foreign protein is a Cannabis plant. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology,* CRC Press, Inc., Boca Raton, 269:284 (1993). Map information concerning chromosomal location is useful for proprietary protection of a subject transgenic plant.

Wang et al. discuss "Large Scale Identification, Mapping and Genotyping of Single-Nucleotide Polymorphisms in the Human Genome," *Science,* 280:1077-1082 (1998), and similar capabilities are becoming increasingly available for the Cannabis genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR, and sequencing, all of which are conventional techniques. SNPs may also be used alone or in combination with other techniques.

Likewise, by means of the present disclosure, plants can be genetically engineered to express various phenotypes of agronomic interest. Through the transformation of Cannabis, the expression of genes can be altered to enhance disease resistance, insect resistance, herbicide resistance, agronomic, grain quality, terpene or cannabinoid content, and other traits. DNA sequences native to Cannabis, as well as non-native DNA sequences, can be transformed into Cannabis and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy et al., *PNAS USA,* 85:8805-8809 (1988); and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan et al., *Bio/Technology,* 12:883-888 (1994); Neuhuber et al., *Mol. Gen. Genet.,* 244:230-241 (1994)); RNA interference (Napoli et al., *Plant Cell,* 2:279-289 (1990); U.S. Pat. No. 5,034,323; Sharp, *Genes Dev.,* 13:139-141 (1999); Zamore et al., *Cell,* 101:25-33 (2000); Montgomery et al., *PNAS USA,* 95:15502-15507 (1998)), virus-induced gene silencing (Burton et al., *Plant Cell,* 12:691-705 (2000); Baulcombe, *Curr. Op. Plant Bio.,* 2:109-113 (1999)); target-RNA-specific ribozymes (Haseloff et al., *Nature,* 334: 585-591 (1988)); hairpin structures (Smith et al., *Nature,* 407:319-320 (2000); WO 99/53050; WO 98/53083); MicroRNA (Aukerman & Sakai, *Plant Cell,* 15:2730-2741 (2003)); ribozymes (Steinecke et al., *EMBO J.,* 11:1525 (1992); Perriman et al., *Antisense Res. Dev.,* 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present disclosure, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with one or more cloned resistance genes to engineer plants that are resistant to specific pathogen strains. See, for example, Jones et al., *Science,* 266:789 (1994) (cloning of the tomato Cf-9 gene for resistance to *Cladosporium flavum*); Martin et al., *Science,* 262:1432 (1993) (tomato Pto gene for resistance to *Pseudomonas syringae* pv. tomato encodes a protein kinase); Mindrinos et al., *Cell,* 78:1089 (1994) (*Arabidopsis* RSP2 gene for resistance to *Pseudomonas syringae*); McDowell & Woffenden, *Trends Biotechnol.,* 21(4):178-83 (2003); and Toyoda et al., *Transgenic Res.,* 11 (6):567-82 (2002).

B. A *Bacillus thuringiensis* protein, a derivative thereof or a synthetic polypeptide modelled thereon. See, for example, Geiser et al., *Gene,* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

C. A lectin. See, for example, Van Damme et al., *Plant Molec. Biol.,* 24:25 (1994), who disclose the nucleotide sequences of several *Clivia miniata* mannose-binding lectin genes.

D. A vitamin-binding protein such as avidin. See, PCT Application US 93/06487, which teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.,* 262:16793 (1987) (nucleotide sequence of rice cysteine proteinase inhibitor); Huub et al., *Plant Molec. Biol.,* 21:985 (1993) (nucleotide sequence of cDNA encoding tobacco proteinase inhibitor I); Sumitani et al., *Biosci. Biotech. Biochem.,* 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

E. An insect-specific hormone or pheromone, such as an ecdysteroid or juvenile hormone, a variant thereof, a mimetic based thereon, or an antagonist or agonist thereof. See, for example, the disclosure by Hammock et al., *Nature*, 344:458 (1990), of baculovirus expression of cloned juvenile hormone esterase, an inactivator of juvenile hormone.

F. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor); Pratt et al., *Biochem. Biophys. Res. Comm.*, 163:1243 (1989) (an allostatin is identified in *Diploptera puntata*); Chattopadhyay et al., *Critical Reviews in Microbiology*, 30(1):33-54 (2004); Zjawiony, *J Nat Prod*, 67(2):300-310 (2004); Carlini & Grossi-de-Sa, *Toxicon*, 40(11):1515-1539 (2002); Ussuf et al., *Curr Sci.*, 80(7):847-853 (2001); Vasconcelos & Oliveira, *Toxicon*, 44(4):385-403 (2004). See also, U.S. Pat. No. 5,266,317 to Tomalski et al., which discloses genes encoding insect-specific, paralytic neurotoxins.

G. An insect-specific venom produced in nature by a snake, a wasp, etc. For example, see, Pang et al., *Gene*, 116:165 (1992), for disclosure of heterologous expression in plants of a gene coding for a scorpion insectotoxic peptide.

H. An enzyme responsible for a hyperaccumulation of a monoterpene, a sesquiterpene, a steroid, hydroxamic acid, a phenylpropanoid derivative, or another non-protein molecule with insecticidal activity.

I. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also, Kramer et al., *Insect Biochem. Molec. BioL*, 23:691 (1993), who teach the nucleotide sequence of a cDNA encoding tobacco hornworm chitinase, and Kawalleck et al., *Plant Molec. Biol.*, 21:673 (1993), who provide the nucleotide sequence of the parsley ubi4-2 polyubiquitin gene, U.S. Pat. Nos. 7,145,060, 7,087,810, and 6,563,020.

J. A molecule that stimulates signal transduction. For example, see the disclosure by Botella et al., *Plant Molec. Biol.*, 24:757 (1994), of nucleotide sequences for mung bean calmodulin cDNA clones, and Griess et al., *Plant Physiol.*, 104:1467 (1994), who provide the nucleotide sequence of a maize calmodulin cDNA clone.

K. A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

L. A membrane permease, a channel former or a channel blocker. For example, see the disclosure of Jaynes et al., *Plant Sci*, 89:43 (1993), of heterologous expression of a cecropin-β lytic peptide analog to render transgenic tobacco plants resistant to *Pseudomonas solanacearum*.

M. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy et al., *Ann. Rev. Phytopathol.*, 28:451 (1990). Coat protein-mediated resistance has been conferred upon transformed plants against alfalfa mosaic virus, cucumber mosaic virus, and tobacco mosaic virus.

N. An insect-specific antibody or an immunotoxin derived therefrom. Thus, an antibody targeted to a critical metabolic function in the insect gut would inactivate an affected enzyme, killing the insect. See, Taylor et al., Abstract #497, Seventh Int'l Symposium on Molecular Plant-Microbe Interactions (Edinburgh, Scotland 1994) (enzymatic inactivation in transgenic tobacco via production of single-chain antibody fragments).

O. A virus-specific antibody. See, for example, Tavladoraki et al., *Nature*, 366:469 (1993), who show that transgenic plants expressing recombinant antibody genes are protected from virus attack.

P. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See, Lamb et al., *Bio/Technology*, 10:1436 (1992). The cloning and characterization of a gene which encodes a bean endopolygalacturonase-inhibiting protein is described by Toubart et al., *Plant 1*, 2:367 (1992).

Q. A developmental-arrestive protein produced in nature by a plant. For example, Logemann et al., *Bio/Technology*, 10:305 (1992), have shown that transgenic plants expressing the barley ribosome-inactivating gene have an increased resistance to fungal disease.

R. Genes involved in the Systemic Acquired Resistance (SAR) Response and/or the pathogenesis-related genes. Briggs, S., *Current Biology*, 5(2) (1995); Pieterse & Van Loon, *Curr. Opin. Plant Bio.*, 7(4):456-64 (2004); and Somssich, *Cell*, 113(7):815-6 (2003).

S. Antifungal genes. See, Cornelissen and Melchers, *Plant Physiol.*, 101:709-712 (1993); Parijs et al., *Planta*, 183:258-264 (1991); and Bushnell et al., *Can. J. of Plant Path.*, 20(2):137-149 (1998). See also, U.S. Pat. No. 6,875,907.

T. Cystatin and cysteine proteinase inhibitors. See, U.S. Pat. No. 7,205,453.

U. Defensin genes. See, WO 03/000863 and U.S. Pat. No. 6,911,577.

Any of the above-listed disease or pest resistance genes can be introduced into the claimed Cannabis variety through a variety of means including, but not limited to, transformation and crossing.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.*, 7:1241 (1988) and Miki et al., *Theor. Appl. Genet.*, 80:449 (1990), respectively.

B. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy propionic acids, and cyclohexanediones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al., also describes genes encoding EPSPS enzymes. See also, U.S. Pat. Nos. 6,566,587, 6,338,961, 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, and 5,491,288; and International Publications EP1173580, WO 01/66704, EP1173581, and EP1173582, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyl-transferase. See, for example, U.S. Pat. No. 7,462,481. A DNA molecule encoding a mutant aroA gene can be obtained under ATCC Accession No. 39256, and the nucleotide sequence of the mutant gene is disclosed in U.S. Pat. No. 4,769,061 to Comai. European Patent Appl. No. 0 333 033 to Kumada et al. and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European Patent Appl. No. 0 242 246 to Leemans et al. DeGreef et al., *Bio/Technology*, 7:61 (1989) describe the production of transgenic plants that express chimeric bar genes coding for phosphinothricin acetyl transferase activity. Exemplary of genes conferring resistance to phenoxy propionic acids and cyclohexanediones, such as sethoxydim and haloxyfop are the Acc1-S1, Acc1-S2, and Acc2-S3 genes described by Marshall et al., *Theor. Appl. Genet.*, 83:435 (1992).

C. An herbicide that inhibits photosynthesis, such as a triazine (psbA and gs+ genes) and a benzonitrile (nitrilase gene). Przibila et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes et al., *Biochem. J.*, 285:173 (1992).

D. Acetohydroxy acid synthase, which has been found to make plants that express this enzyme resistant to multiple types of herbicides, has been introduced into a variety of plants. See, Hattori et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17 (1994)); genes for glutathione reductase and superoxide dismutase (Aono et al., *Plant Cell Physiol.*, 36:1687 (1995)); and genes for various phosphotransferases (Datta et al., *Plant Mol. Biol.*, 20:619 (1992)).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes can be introduced into the claimed Cannabis variety through a variety of means including but not limited to transformation and crossing.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon et al., *Proc. Natl. Acad. Sci. USA*, 89:2625 (1992).

B. Modified carbohydrate composition effected, for example, by transforming plants with a gene coding for an enzyme that alters the branching pattern of starch, or a gene altering thioredoxin, such as NTR and/or TRX (see, U.S. Pat. No. 6,531,648, which is incorporated by reference for this purpose), and/or a gamma zein knock out or mutant, such as cs27 or TUSC27 or en27 (see, U.S. Pat. Nos. 6,858,778 and 7,741,533 and U.S. Publ. No. 2005/0160488, which are incorporated by reference for this purpose). See, Shiroza et al., *J. Bacteriol.*, 170:810 (1988) (nucleotide sequence of *Streptococcus mutans* fructosyltransferase gene); Steinmetz et al., *Mol. Gen. Genet.*, 200:220 (1985) (nucleotide sequence of *Bacillus subtilis* levansucrase gene); Pen et al., *Bio/Technology*, 10:292 (1992) (production of transgenic plants that express *Bacillus licheniformis* alpha-amylase); Elliot et al., *Plant Molec. Biol.*, 21:515 (1993) (nucleotide sequences of tomato invertase genes); Sogaard et al., *J. Biol. Chem.*, 268:22480 (1993) (site-directed mutagenesis of barley alpha-amylase gene); Fisher et al., *Plant Physiol.*, 102:1045 (1993) (maize endosperm starch branching enzyme II); WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

C. Altering conjugated linolenic or linoleic acid content, such as in WO 01/12800. Altering LEC1, AGP, Dek1, Superal1, mi1ps, and various Ipa genes, such as Ipa1, Ipa3, hpt, or hggt. See, for example, WO 02/42424, WO 98/22604, WO 03/011015, WO 02/057439, WO 03/011015, U.S. Pat. Nos. 6,423,886, 6,197,561, 6,825,397, 7,157,621, U.S. Publ. No. 2003/0079247, and Rivera-Madrid, R. et al., *Proc. Natl. Acad. Sci.*, 92:5620-5624 (1995).

D. Altered essential seed amino acids. See, for example, U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); U.S. Pat. No. 5,850,016 (alteration of amino acid compositions in seeds); U.S. Pat. No. 5,885,802 (high methionine); U.S. Pat. No. 5,885,801 (high threonine); U.S. Pat. No. 6,664,445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 7,098,381 (UDPGdH); U.S. Pat. No. 6,194,638 (RGP); U.S. Pat. Nos. 6,399,859, 6,930,225, 7,179,955, and 6,803,498; U.S. Publ. No. 2004/0068767; WO 99/40209 (alteration of amino acid compositions in seeds); WO 99/29882 (methods for altering amino acid content of proteins); WO 98/20133 (proteins with enhanced levels of essential amino acids); WO 98/56935 (plant amino acid biosynthetic enzymes); WO 98/45458 (engineered seed protein having higher percentage of essential amino acids); WO 98/42831 (increased lysine); WO 96/01905 (increased threonine); WO 95/15392 (increased lysine); WO 01/79516; and WO 00/09706 (Ces A: cellulose synthase).

4. Genes that Control Male Sterility:

There are several methods of conferring genetic male sterility available, such as multiple mutant genes at separate locations within the genome that confer male sterility, as disclosed in U.S. Pat. Nos. 4,654,465 and 4,727,219 to Brar et al., and chromosomal translocations as described by Patterson in U.S. Pat. Nos. 3,861,709 and 3,710,511. In addition to these methods, Albertsen et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. Introduction of a deacetylase gene under the control of a tapetum-specific promoter and with the application of the chemical N-Ac-PPT. See, International Publication WO 01/29237.

B. Introduction of various stamen-specific promoters. See, International Publications WO 92/13956 and WO 92/13957.

C. Introduction of the barnase and the barstar genes. See, Paul et al., *Plant Mol. Biol.,* 19:611-622 (1992).

For additional examples of nuclear male and female sterility systems and genes, see also, U.S. Pat. Nos. 5,859, 341, 6,297,426, 5,478,369, 5,824,524, 5,850,014, and 6,265, 640, all of which are hereby incorporated by reference.

5. Genes that Create a Site for Site Specific DNA Integration:

This includes the introduction of FRT sites that may be used in the FLP/FRT system and/or Lox sites that may be used in the Cre/loxP system. See, for example, Lyznik et al., Site-Specific Recombination for Genetic Engineering in Plants, *Plant Cell Rep,* 21:925-932 (2003) and WO 99/25821, which are hereby incorporated by reference. Other systems that may be used include the Gin recombinase of phage Mu (Maeser et al. (1991); Vicki Chandler, The Maize Handbook, Ch. 118 (Springer-Verlag 1994)); the Pin recombinase of *E. coli* (Enomoto et al. (1983)); and the R/RS system of the pSR1 plasmid (Araki et al. (1992)).

6. Genes that Affect Abiotic Stress Resistance:

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Methods for Cannabis Transformation

Numerous methods for plant transformation have been developed including biological and physical plant transformation protocols. See, for example, Miki et al., "Procedures for Introducing Foreign DNA into Plants," in *Methods in Plant Molecular Biology and Biotechnology,* Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber et al., "Vectors for Plant Transformation," in *Methods in Plant Molecular Biology and Biotechnology,* Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium.* See, for example, Horsch et al., *Science,* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports,* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.*, 5:27 (1987); Sanford, J. C., *Trends Biotech.*, 6:299 (1988); Klein et al., *Bio/Tech.*, 6:559-563 (1988); Sanford, J. C., *Physiol Plant*, 7:206 (1990); Klein et al., *Biotechnology*, 10:268 (1992). See also, U.S. Pat. No. 5,015,580 (Christou et al.), issued May 14, 1991 and U.S. Pat. No. 5,322,783 (Tomes et al.), issued Jun. 21, 1994.

Another method for physical delivery of DNA to plants is sonication of target cells. Zhang et al., *Bio/Technology*, 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA*, 84:3962 (1987). Direct uptake of DNA into protoplasts using $CaCl_2$) precipitation, polyvinyl alcohol or poly-L-ornithine have also been reported. Hain et al., *Mol. Gen. Genet.*, 199:161 (1985) and Draper et al., *Plant Cell Physiol.*, 23:451 (1982). Electroporation of protoplasts and whole cells and tissues have also been described (Donn et al., In Abstracts of VIII' International Congress on Plant Cell and Tissue Culture IAPTC, A2-38, p. 53 (1990); D'Halluin et al., *Plant Cell*, 4:1495-1505 (1992); and Spencer et al., *Plant Mol. Biol.*, 24:51-61 (1994)).

Following transformation of Cannabis target tissues, expression of the above-described selectable marker genes allows for preferential selection of transformed cells, tissues, and/or plants, using regeneration and selection methods well known in the art.

The foregoing methods for transformation would typically be used for producing a transgenic cultivar. The transgenic cultivar could then be crossed with another (non-transformed or transformed) cultivar in order to produce a new transgenic cultivar. Alternatively, a genetic trait that has been engineered into a particular Cannabis line using the foregoing transformation techniques could be moved into another line using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar or cultivars that do not contain that gene. As used herein, "crossing" can refer to a simple x by y cross or the process of backcrossing depending on the context.

Genetic Marker Profiles

In addition to phenotypic observations, a plant can also be identified by its genotype. The genotype of a plant can be characterized through a genetic marker profile which can identify plants of the same cultivar, or a related cultivar, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs). For example, see, Cregan et al., "An Integrated Genetic Linkage Map of the Soybean Genome," *Crop Science*, 39:1464-1490 (1999) and Berry et al., "Assessing Probability of Ancestry Using Simple Sequence Repeat Profiles: Applications to Maize Inbred Lines and Soybean Varieties," *Genetics*, 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for Cannabis variety NWG 4113. In addition to being used for identification of Cannabis variety NWG 4113, and plant parts and plant cells of Cannabis variety NWG 4113, the genetic profile may be used to identify a Cannabis plant produced through the use of Cannabis variety NWG 4113 or to verify a pedigree for progeny plants produced through the use of Cannabis variety NWG 4113. The genetic marker profile is also useful in breeding and developing backcross conversions.

The present disclosure provides in one embodiment a Cannabis plant variety characterized by molecular and physiological data obtained from the representative sample of the variety deposited with the Provasoli-Guillard National Center for Marine Algae and Microbiota (NCMA). Further provided by the disclosure is a Cannabis plant formed by the combination of the disclosed Cannabis plant or plant cell with another Cannabis plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by polymerase chain reaction (PCR), thereby eliminating the need for labor-intensive Southern hybridization. PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all profiles are performed in the same lab.

A genetic marker profile of Cannabis variety NWG 4113 can be used to identify plants comprising Cannabis variety NWG 4113 as a parent, since such plants will comprise the same homozygous alleles as Cannabis variety NWG 4113. Because the Cannabis variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of Cannabis variety NWG 4113 in their development, such as Cannabis variety NWG 4113 comprising a backcross conversion or transgene, may be identified by having a molecular marker profile with a high percent identity to Cannabis variety NWG 4113. Such a percent identity might be 95%, 96%, 97%, 98%, 99%, 99.5%, or 99.9% identical to Cannabis variety NWG 4113.

A genetic marker profile of Cannabis variety NWG 4113 can also be used to identify essentially derived varieties and other progeny varieties developed from the use of Cannabis variety NWG 4113, as well as cells and other plant parts thereof. Progeny plants and plant parts produced using Cannabis variety NWG 4113 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from Cannabis variety NWG 4113, as measured by either percent identity or percent similarity. Such progeny may be further characterized as being within a pedigree distance of Cannabis variety NWG 4113, such as within 1, 2, 3, 4, or 5 or less crosspollinations to a Cannabis plant other than Cannabis variety NWG 4113 or a plant that has Cannabis variety NWG 4113 as a progenitor. Unique molecular profiles may be identified with other molecular tools such as SNPs and RFLPs.

Gene Conversions

When the term "Cannabis plant" is used in the context of the present disclosure, this also includes a gene conversion of that variety. The term gene converted plant as used herein refers to those Cannabis plants which are developed by a plant breeding technique called backcrossing wherein essentially all of the desired morphological and physiological characteristics of a variety are recovered in addition to the gene transferred into the line via the backcrossing technique. By "essentially all" as used herein in the context of morphological and physiological characteristics it is meant that the characteristics of a plant are recovered that are otherwise present when compared in the same environment, other than occasional variant traits that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

Backcrossing methods can be used with the present disclosure to improve or introduce a characteristic into the cultivar. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental Cannabis plant that contributes the gene for the desired characteristic is termed the nonrecurrent or donor parent. This terminology refers to the fact that the nonrecurrent parent is used one time in the backcross protocol and therefore does not recur. The parental Cannabis plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original cultivar of interest (recurrent parent) is crossed to a second cultivar (nonrecurrent parent) that carries the single gene of interest to be transferred. The resulting progeny from this cross are then crossed again to the recurrent parent and the process is repeated until a Cannabis plant is obtained wherein essentially all of the morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute traits or characteristics in the original line. To accomplish this, a gene or genes of the recurrent cultivar are modified or substituted with the desired gene or genes from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait or traits to the plant. The exact backcrossing protocol will depend on the characteristics or traits being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected for in the development of a new line but that can be improved by backcrossing techniques. Gene traits may or may not be transgenic, examples of these traits include but are not limited to, herbicide resistance, resistance for bacterial, fungal, or viral disease, insect resistance, industrial usage, yield stability, yield enhancement, male sterility, modified oil content, or modified terpene or cannabinoid content. These genes are generally inherited through the nucleus. Several of these gene traits are described in U.S. Pat. Nos. 5,777,196; 5,948,957 and 5,969,212, the disclosures of which are specifically hereby incorporated by reference.

Tilling

TILLING (Targeting Induced Local Lesions IN Genomes) can be used to produce plants in which endogenous genes comprise a mutation. In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time. For a TILLING assay, heteroduplex methods using specific endonucleases can be used to detect single nucleotide polymorphisms (SNPs). Alternatively, Next Generation Sequencing of DNA from pools of mutagenised plants can be used to identify mutants in the gene of choice. Typically, a mutation frequency of one mutant per 1000 plants in the mutagenised population is achieved. Using this approach, many thousands of plants can be screened to identify any individual with a single base change as well as small insertions or deletions (1-30 bp) in any gene or specific region of the genome. TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Genome Editing

Genome editing uses engineered nucleases such as RNA guided DNA endonucleases or nucleases composed of sequence specific DNA binding domains fused to a non-specific DNA cleavage module. These engineered nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption. Engineered nucleases useful in the methods of the present disclosure include zinc finger nucleases (ZFNs), transcription activator-like (TAL) effector nucleases (TALEN) and CRISPR/Cas9 type nucleases.

Typically, nuclease encoded genes are delivered into cells by plasmid DNA, viral vectors or in vitro transcribed mRNA. A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the Cis2His2 type of zinc finger that is very generally represented, for example, by the zinc finger transcription factors TFIIIA or Sp1. In a preferred embodiment, the zinc finger domain comprises three Cis2His2 type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques (see, for example, Bibikova et al., 2002).

The ZFN DNA-cleavage domain is derived from a class of non-specific DNA cleavage domains, for example the DNA-cleavage domain of a Type II restriction enzyme such as FoId (Kim et al., 1996). Other useful endonucleases may include, for example, HhaI, HindIII, Nod, BbvCI, EcoRI, BglI, and AlwI.

A transcription activator-like (TAL) effector nuclease (TALEN) comprises a TAL effector DNA binding domain and an endonuclease domain. TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FoId (Kim et al., 1996). Other useful endonucleases may include, for example, HhaI, HindIII, Nod, BbvCI, EcoRI, BglI, and AhvI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Distinct from the site-specific nucleases described above, the clustered regulatory interspaced short palindromic repeats (CRISPR)/Cas system provides an alternative to ZFNs and TALENs for inducing targeted genetic alterations, via RNA-guided DNA cleavage.

CRISPR systems rely on CRISPR RNA (crRNA) and transactivating chimeric RNA (tracrRNA) for sequence-specific cleavage of DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

Tissue Culture

Further reproduction of the variety can occur by tissue culture and regeneration. Tissue culture of various tissues and regeneration of plants therefrom is well known and widely published. For example, reference may be had to Komatsuda, T. et al., *Crop Sci.*, 31:333-337 (1991); Stephens, P. A. et al., *Theor. Appl. Genet.*, 82:633-635 (1991); Komatsuda, T. et al., *Plant Cell, Tissue and Organ Culture*, 28:103-113 (1992); Dhir, S. et al., *Plant Cell Reports*, 11:285-289 (1992); Pandey, P. et al., *Japan J. Breed.*, 42:1-5 (1992); and Shetty, K. et al., *Plant Science*, 81:245-251 (1992); as well as U.S. Pat. No. 5,024,944, issued Jun. 18, 1991 to Collins et al. and U.S. Pat. No. 5,008,200, issued Apr. 16, 1991 to Ranch et al. Thus, another aspect of this disclosure is to provide cells which upon growth and differentiation produce Cannabis plants having the morphological and physiological characteristics of Cannabis variety NWG 4113.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Vegetative Propagation

A Cannabis plant can also be propagated vegetatively. For most cannabinoid producing purposes, only female plants are desired. The presence of male flowers is considered undesirable as pollination is known to reduce the cannabinoid yield. For this reason, Cannabis is also grown through vegetative (i.e., asexual) propagation. In this way, only female plants are produced and space or resources are not wasted on male plants.

A part of the plant, for example a shoot tissue, is collected, and a new plant is obtained from the part. Such part typically comprises an apical meristem of the plant. The collected part is transferred to a medium allowing development of a plantlet, including for example rooting or development of shoots. This is achieved using methods well known in the art. For example, a stem cutting containing one or more nodal segments and leaves may be used. Rooting hormone is applied to the base of cutting to promote rooting before planting in soil. Rooting typically initiates in 2 to 3 weeks. Eight-week old rooted plants are normally ready to be transplanted. Plants are exposed to long photoperiods (normally greater than 12 h, 18 hours, or 24 hours) to maintain vegetative growth or exposed to a photoperiod less than 12 hours to induce flowering. See, Chandra et al., *Front Plant Sci.* 2020 Jun. 26; 11:958.

Accordingly, methods of vegetatively propagating a plant of Cannabis variety NWG 4113 are provided. The methods may comprise collecting tissue capable of being propagated from a plant of Cannabis variety NWG 4113, cultivating the tissue to obtain proliferated shoots, and rooting the proliferated shoots to obtain rooted plantlets. Optionally the methods may further comprise growing plants from the rooted plantlets. In certain embodiments, the tissue capable of being propagated is a stem cutting. Plantlets and plants (i.e., asexual clones) produced by these methods, are encompassed by the disclosure.

Additional Breeding Methods

This disclosure is directed to methods for producing a Cannabis plant by crossing a first parent Cannabis plant with a second parent Cannabis plant wherein either the first or second parent Cannabis plant is variety NWG 4113. The other parent may be any other Cannabis plant. Any such methods using Cannabis variety NWG 4113 are part of this disclosure: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, Principles of Plant Breeding (1960); Simmonds, Principles of Crop Improvement (1979); Sneep et al. (1979); Fehr, "Breeding Methods for Cultivar Development," Chapter 7, Soybean Improvement, Production and Uses, 2nd ed., Wilcox editor (1987)).

The following describes breeding methods that may be used with Cannabis variety NWG 4113 in the development of further Cannabis plants. One such embodiment is a method for developing a variety NWG 4113 progeny Cannabis plant in a Cannabis plant breeding program comprising: obtaining the Cannabis plant, or a part thereof, of variety NWG 4113, utilizing the plant, or plant part, as a source of breeding material, and selecting a Cannabis variety NWG 4113 progeny plant with molecular markers in common with variety NWG 4113 and/or with morphological and/or physiological characteristics selected from the characteristics listed in Table 1. Breeding steps that may be used in the Cannabis plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of Cannabis variety NWG 4113 progeny Cannabis plants, comprising crossing variety NWG 4113 with another Cannabis plant, thereby producing a population of Cannabis plants which, on average, derive 50% of their alleles from Cannabis variety NWG 4113. A plant of this population may be selected and repeatedly selfed or sibbed with a Cannabis cultivar resulting from these successive filial generations. One embodiment of this disclosure is the Cannabis cultivar produced by this method and that has obtained at least 50% of its alleles from Cannabis variety NWG 4113.

One of ordinary skill in the art of plant breeding would know how to evaluate the traits of two plant varieties to determine if there is no significant difference between the two traits expressed by those varieties. For example, see, Fehr and Walt, *Principles of Cultivar Development*, pp. 261-286 (1987). Thus the disclosure includes Cannabis variety NWG 4113 progeny Cannabis plants comprising a combination of at least two variety NWG 4113 traits selected from those listed in Table 1, so that the progeny Cannabis plant is not significantly different for the traits than Cannabis variety NWG 4113 as determined at the 5% significance level when grown in the same environmental conditions. Using techniques described herein, molecular markers may be used to identify the progeny plant as a Cannabis variety NWG 4113 progeny plant. Mean trait values may be used to determine whether trait differences are significant, and preferably the traits are measured on plants grown under the same environmental conditions. Once such a cultivar is developed, its value is substantial since it is important to advance the germplasm base as a whole in order to maintain or improve traits such as yield, disease resistance, pest resistance, and plant performance in extreme environmental conditions.

Progeny of Cannabis variety NWG 4113 may also be characterized through their filial relationship with Cannabis variety NWG 4113, as for example, being within a certain number of breeding crosses of Cannabis variety NWG 4113. A breeding cross is a cross made to introduce new genetics into the progeny, and is distinguished from a cross, such as a self or a sib cross, made to select among existing genetic alleles. The lower the number of breeding crosses in the pedigree, the closer the relationship between Cannabis variety NWG 4113 and its progeny. For example, progeny produced by the methods described herein may be within 1, 2, 3, 4, or 5 breeding crosses of Cannabis variety NWG 4113.

Uses of Cannabis Variety NWG 4113

Cannabis variety NWG 4113 may be used as a source for cannabinoids, terpenoids, and other compounds. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *cannabis* plant (Rudolf Brenneisen, 2007, Chemistry and Analysis of Phytocannabinoids (cannabinoids produced by *cannabis*) and other Cannabis Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from Cannabis sativa L", Pharmacology Biochemistry and Behavior 95 (4): 434-42; incorporated herein by reference). The two cannabinoids usually produced in greatest abundance are cannabidiol (CBD) and/or Δ-9-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in Cannabis.

Cannabinoids are the most studied group of secondary metabolites in Cannabis. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

The cannabinoids in cannabis plants include, but are not limited to, Δ9 Tetrahydrocannabinol (Δ9-THC), Δ. 8-Tetrahydrocannabinol (Δ8-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), Δ.9-Tetrahydrocannabivarin (THCV), cannabichromevarin (CBCV), and cannabigerovarin (CBGV). See Holley et al. (Constituents of Cannabis *sativa* L. XI Cannabidiol and cannabichromene in samples of known geographical origin, J. Pharm. Sci. 64:892-894, 1975) and De Zeeuw et al. (Cannabinoids with a propyl side chain in Cannabis, Occurrence and chromatographic behavior, Science 175:778-779), each of which is herein incorporated by reference in its entirety for all purposes. Non-THC cannabinoids can be collectively referred to as "CBs", wherein CBs can be one of THCV, CBDV, CBGV, CBCV, CBD, CBC, CBE, CBG, CBN, CBND, and CBT cannabinoids.

Cannabis variety NWG 4113 may be used in human food products as well as animal feed. When referring to food is meant any edible material that comprises the Cannabis plant or plant part or extract or combinations thereof. It includes food that can be eaten or beverages that may be drunk. In certain embodiments, such as when used as a supplement, there may be included ingredients that are consumed with the plant material that pass through the digestive system, such as capsules or similar ingredients. Feed is likewise any edible material intended for non-human animals that comprises the Cannabis plant or plant part or extract or combinations thereof.

The plant and any part thereof and extracts thereof can be useful in a wide variety of food and feed uses. The food or feed can comprise the Cannabis plant or plant part. Hemp seed (grain), for example, is high in protein, non-intoxicating and can be used whole, chopped, crushed, or ground into flour, or pressed and used to produce, by way of example without limitation, various food additives, vegetable burgers, cereals, milk, butter, cheese, salad dressings and more. It can be consumed raw or cooked. The ground seed can be used to produce flour for use in breads, pasta and the like. Juice may be pressed from the leaf or other parts of the plant and can be mixed in food and used in beverages, for example. Since hemp has a high protein content it is used to produce edible food protein sources, such as bars and drinks. See, e.g., US patent application 20150173395. (This reference and all references cited herein are incorporated herein by reference.) The flowers of the plant are high in flavonoids, carotenoids, terpenoids and cannabinoids. Hemp resin may also be produced by extraction of hemp flowers.

A variety of extracts can be obtained, including, for example, oil as well as kief, which is the trichomes of cannabis and rich in cannabinoid and terpenes. When pressed it is referred to as hash or hashish and can be pressed into a solid phase. Bubble hash is produced by placing cannabis material in a cold water bath and stirring to produce hash with paste-like properties. Solvent reduced oils can be produced by soaking plant material in a chemical solvent, then boiling or evaporating the solvent. Oil that remains is an example of one extract. Tinctures are alcoholic extracts of cannabis, where e-juice refers to extracts dissolved in propylene glycol, vegetable glycerin or a combination. Many various extracts can be obtained that are useful in food and feed and the above is not intended to be limiting.

Oil produced from hemp seed has a vast array of applications. It may be extracted in any convenient methods (such as those described herein) and even powdered, for use in beverages, baked goods and supplements (See, e.g., US Patent Application No. 20190090515). Hemp meal or fractions thereof can be used in food and feed. Products containing cannabidiol have shown an immense growth and are used in a variety of edible products including supplements.

Primary proteins of the seed are globulin edestin (60-80%), a storage protein having high levels of arginine and glutamic acids, and albumin. For example, see Callaway (2004) "Hempseed as nutritional resource: An overview" *Euphytica* 140 (1-2) 65-72. The result is a protein source having all or nearly all essential amino acids and that is easy to digest. Other amino acids found include asparagine, threonine, serine, glutamate/glutamine, proline, glycine, alanine, cysteine, valine, methionine, isoleucine, leucine, tyrosine, phenylalanine, histidine, lysine, arginine and tryptophan. Vitamins and minerals in hemp seed include vitamin E, thiamine, riboflavin, phosphorous, potassium, magnesium, calcium, iron, sodium, manganese, zinc and copper.

Whether used as food or feed, the plant, plant part or extract can be delivered raw, dried, freeze dried, chopped, ground, powdered, filtered, cleaned and/or combined with at least one excipient, carrier, diluent or an edible compound. The edible compound may be a compound that is edible by a human animal, for food, or a non-human animal, for feed. Examples of edible feed compounds include a wide variety of compounds, and can include such compounds as plant, plant parts or oil of corn, soybean, oats, alfalfa, wheat or barley, by way of example without limitation. The compounds edible by human can be any compound that can be consumed by a human. The carrier, excipient and/or diluent can provide improved properties of the composition, such as standardizing, preserving and stabilizing and improve delivery. A myriad of such excipients, carriers and diluents are available to a person of skill in the art. Without intending to be limiting, examples include wetting agents, lubricating agents, preservatives (sodium chloride, potassium sorbate, calcium are among examples), lipids, stabilizers, solubilizers and emulsifiers (examples of emulsifiers and surfactants include polysorbates, acetylated monoglycerides, monooleates, polyglyceryl fatty acids). An embodiment provides the excipient, carrier or diluent comprises water and an excipient, carrier or diluent that is not water.

Cannabis variety NWG 4113 may be used for fiber. Cannabis has had high value for thousands of years in the use of its fiber. Hemp fibers are durable fibers that are harvested from plants of the *Cannabis* genus, for example. The term hemp may also be used to identify the entire plant from which hemp fibers are derived. The hemp fibers are considered to be a commercially valuable part of the hemp plant. Bast fibers give the plants its strength. The term "bast fibers" refers to the fibers that grow on the outside of the woody interior of the plant's stalk and under the bark. In the hemp plant, bast fibers grow to be approximately 3 feet to 15 feet long and are used for industrial purposes including paper, textiles, biodegradable plastics, construction, health food and fuel. Hemp is an important source of fibers because it is one of the faster growing biomasses. For example, hemp farming may produce up to 25 tons of dry matter per hectare per year. The dry matter can include, by way of example, approximately, one ton of hemp bast fiber per 3-4 tons of the dry retted hemp straw. The chemical composition of natural fibers consists essentially of cellulose (microfiber of the cell wall), hemicelluloses, and lignin (biopolymer components of the cell wall). The outer surfaces of plant fiber contain waxes, fats, and pectin. The cellulose group is a highly crystalline structure. Hemp is particularly useful as fiber in that the primary bast fibers in the bark are long, in some examples 5-40 mm long and are present in fiber bundles which can be 1-5 m long. Secondary bast (phloem) fibers are approximately 2 mm long.

The fibers may be used in a wide variety of applications. The fiber can be used, by way of example without limitation, in producing textiles including use in clothing made from hemp fiber and in producing pulp and paper products, which last longer than tree paper and use less toxic chemicals in production. Other examples include use to produce rope, fiberboard, and construction materials. Fiber can be used for composites for industrial uses. Additional examples include animal bedding, geotextiles (including agricultural textiles such as matting to prevent soil erosion, ground covers to reduce weeds and the like). In still further examples, hemp can be used to produce a reinforced composition material. See U.S. Pat. No. 9,187,624, incorporated herein by reference. The composite material may be used, for example, as building and infrastructure material or high-performance structural material; as a composite material for wood flooring; to produce pallets; as packaging including pharmaceutical product packaging; building and infrastructure applications; bridge decking, and in retaining walls to replace the conventional materials, especially the pressured treated lumbers and wood plastic composites.

The fibers can in an embodiment be processed, such as by washing, drying, drying under vacuum and heat, by cleaning, combing, carding, pulping, chopping, weaving, and spinning, for example, and/or chemical processed such as, but not limited to, by steam treatment, alkalization, dyeing, and/or other chemical treatment to provide any desired properties, for example. In certain embodiments, the hemp fibers are cut or chopped. In still further examples hemp stalks may be reduced into particulate hemp which may include bast fiber and shive (woody core) and in another example can be further reduced to crumbs. Further forms include, for example, hemp fines or flour or pellets. See U.S. Pat. No. 10,052,636. In another example extracting hemp fibers from decorticated hemp provides for yet further useful products. See U.S. Pat. No. 8,591,701.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

DEPOSITS

Applicant has made a deposit of at least 625 seeds of Cannabis variety NWG 4113 with the Provasoli-Guillard National Center for Marine Algae and Microbiota (NCMA), 60 Bigelow Drive, East Boothbay, Me. 04544, USA, with NCMA Accession No. 202204003. The seeds deposited with the NCMA on Apr. 7, 2022 were taken from the deposit maintained by New West Genetics, PO Box 1662, Fort Collins, Colorado 80522 since prior to the filing date of this application. Access to this deposit will be available during the pendency of the application to the Commissioner of Patents and Trademarks and persons determined by the Commissioner to be entitled thereto upon request. Upon issue of claims, the Applicant(s) will make available to the public, pursuant to 37 CFR 1.808, a deposit of at least 625 seeds of Cannabis variety NWG 4113 with the NCMA. This deposit will be maintained in the depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§ 1.801-1.809, including providing an indication of the viability of the sample. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.).

What is claimed is:

1. A seed of Cannabis variety NWG 4113, wherein a sample of seed of the variety was deposited under NCMA Accession No. 202204003.

2. A Cannabis plant produced by growing the seed of claim 1.

3. A Cannabis plant, or a part thereof, having all the physiological and morphological characteristics of the Cannabis plant of claim 2.

4. A part of the Cannabis plant of claim 2, wherein the part is a microspore, pollen, an ovary, an ovule, an embryo sac, an egg cell, a cutting, a root, a leaf, an inflorescence, a stem, a trichome, a cell, or a protoplast.

5. A tissue culture of regenerable cells or protoplasts from the Cannabis plant of claim 2.

6. The tissue culture of claim 5, wherein the cells of the tissue culture are produced from a plant part selected from the group of embryo, meristematic cell, leaf, cotyledon, hypocotyl, stem, root, root tip, pistil, anther, flower, seed, and pollen.

7. A Cannabis plant regenerated from the tissue culture of claim 5, wherein the plant has all of the morphological and physiological characteristics of variety NWG 4113, wherein a sample of seed of the variety was deposited under NCMA Accession No. 202204003.

8. A method of vegetatively propagating a plant of Cannabis variety NWG 4113, the method comprising:
(a) collecting tissue capable of being propagated from a plant of Cannabis variety NWG 4413, wherein a sample of seed of the variety was deposited under NCMA Accession No. 202204003;
(b) cultivating the tissue to obtain proliferated shoots; and
(c) rooting the proliferated shoots to obtain a rooted plantlet.

9. The method of claim 8, further comprising growing a plant from the rooted plantlet.

10. A method for producing a progeny plant of Cannabis variety NWG 4113, comprising:
crossing a Cannabis plant of variety NWG 4113 with itself or with another Cannabis plant;
harvesting the resultant seed; and
growing the seed.

11. A method for producing a hybrid Cannabis seed, wherein the method comprises:
crossing the Cannabis plant of claim 2 with a plant of a different Cannabis variety; and
harvesting the resultant $F_1$ hybrid Cannabis seed.

12. A hybrid Cannabis seed produced by the method of claim 11.

13. A hybrid Cannabis plant, or a part thereof, produced by growing the hybrid Cannabis seed of claim 12.

14. A method of producing a Cannabis plant derived from Cannabis variety NWG 4113, the method comprising the steps of:
(a) crossing the plant of claim 2 with a second Cannabis plant to produce a progeny plant;
(b) crossing the progeny plant of step (a) with itself or the second Cannabis plant in step (a) to produce a seed;
(c) growing a progeny plant of a subsequent generation from the seed produced in step (b);
(d) crossing the progeny plant of a subsequent generation of step (c) with itself or the second Cannabis plant in step (a) to produce a Cannabis plant derived from Cannabis variety NWG 4113.

15. A method of introducing a desired trait into Cannabis variety NWG 4113, the method comprising:
(a) crossing a plant of Cannabis variety NWG 4113, wherein a representative sample of seed was deposited under NCMA Accession No. 202204003, with a plant of another Cannabis variety that comprises the desired trait to produce an $F_1$ progeny plant;
(b) selecting at least a first progeny plant that comprises the desired trait to produce a selected progeny plant;
(c) crossing the selected progeny plant with a plant of Cannabis variety NWG 4113 to produce at least a first backcross progeny plant that comprises the desired trait;
(d) selecting for at least one backcross progeny plant that has the desired trait and otherwise all of the physiological and morphological characteristics of a plant of Cannabis variety NWG 4113 to produce at least one selected backcross progeny plant; and
(e) repeating steps (c) and (d) three or more times in succession to produce a selected fourth or higher backcross progeny plant that comprises the desired trait and otherwise all of the physiological and morphological characteristics of a plant of Cannabis variety NWG 4113.

16. The method of claim 15, wherein the desired trait is herbicide resistance, insect resistance, resistance to bacterial disease, fungal disease, or viral disease, male sterility, modified oil content, or modified terpene or cannabinoid content.

17. A Cannabis plant produced by the method of claim 15, wherein the plant comprises the desired trait and otherwise comprises all of the physiological and morphological characteristics of a plant of Cannabis variety NWG 4113.

18. A method of producing a plant of Cannabis variety NWG 4113 comprising at least one new trait, the method comprising:
introducing a transgene conferring the at least one new trait into a plant of Cannabis variety NWG 4113, wherein a sample of seed of the variety has been deposited under NCMA Accession No. 202204003.

19. The method of claim 18, wherein the new trait is herbicide resistance, insect resistance, resistance to bacterial disease, fungal disease, or viral disease, male sterility, modified oil content, or modified terpene or cannabinoid content.

20. A Cannabis plant produced by the method of claim 19, wherein the plant comprises the new trait and otherwise comprises all of the physiological and morphological characteristics of a plant of Cannabis variety NWG 4113.

21. A method of introducing a mutation into the genome of Cannabis variety NWG 4113, the method comprising applying a mutagen to the plant of claim 1, or a part thereof, wherein the mutagen is selected from ethyl methanesulfonate, gamma-rays, and sodium azide, and wherein the resulting plant comprises a genome mutation.

22. A plant of Cannabis variety NWG 4113, a sample of seed of the variety having been deposited under NCMA Accession No. 202204003, wherein the plant further comprises at least one locus conversion, wherein the locus conversion confers the plant with a trait selected from male sterility, herbicide resistance, insect resistance, disease resistance, modified oil content, or modified terpene or cannabinoid content.

23. A method of producing a genetically modified Cannabis plant, wherein the method comprises mutation, transformation, gene conversion, genome editing, RNA interference or gene silencing of the plant of claim 2.

24. A method of conferring aroma, flavoring, or desired health benefits to a beverage, the method comprising:
preparing the beverage with the Cannabis plant of claim 2, or a part thereof, or a composition purified therefrom.

25. The method of claim 24, wherein the beverage is beer, wine, cider, distilled spirit, hard soda, soft drink, juice, water, or flavored water.

26. A method of preparing cannabinoid isolates or isolate formulations, the method comprising:

harvesting flower tissue from the Cannabis plant of claim 2; and extracting cannabinoids from the flower tissue.

27. A method of producing a commodity plant product, the method comprising obtaining the plant of claim 2 or a part thereof and producing the commodity plant product therefrom.

28. A method of comparing and/or characterizing the genotype of a plant of Cannabis variety NWG 4113, a sample of seed of which has been deposited under NCMA Accession No. 202204003, comprising:

obtaining a sample of nucleic acids from the plant of Cannabis variety NWG 4113;

obtaining a sample of nucleic acids from a plant of a reference Cannabis variety;

comparing the nucleic acids obtained from the plant of Cannabis variety NWG 4113 to the sample of nucleic acids obtained from the reference plant, and detecting a plurality of polymorphisms between the two nucleic acid samples, wherein the plurality of polymorphisms is indicative of Cannabis variety NWG 4113 and/or gives rise to the expression of any one or more, or all, of the physiological and morphological characteristics of Cannabis variety NWG 4113.

29. A method for developing a Cannabis variety in a Cannabis plant breeding program, comprising applying plant breeding techniques comprising recurrent selection, backcrossing, pedigree breeding, marker enhanced selection, mutation breeding, or genetic modification to the Cannabis plant of claim 2, or its parts, to develop of a Cannabis variety.

* * * * *